United States Patent [19]

Cleary

[11] 4,408,989
[45] Oct. 11, 1983

[54] ORTHODONTIC PALATAL ARCH WIRES FOR ACCURATE TRANSMITTAL OF CORRECTIONAL FORCES

[75] Inventor: James D. Cleary, Monrovia, Calif.
[73] Assignee: Unitek Corporation, Monrovia, Calif.
[21] Appl. No.: 345,983
[22] Filed: Feb. 5, 1982
[51] Int. Cl.³ .............................................. A61C 7/00
[52] U.S. Cl. ...................................................... 433/7
[58] Field of Search .................................. 433/6, 7, 17

[56] References Cited

U.S. PATENT DOCUMENTS 3,792,529  2/1974  Goshgarian ............................ 433/7
4,202,100  5/1980  Forster ................................... 433/7

*Primary Examiner*—Robert Peshock
*Attorney, Agent, or Firm*—Stuart E. Krieger; Richard H. Brink; Isaac Jarkovsky

[57] ABSTRACT

An orthodontal palatal arch wire is provided for directional control over a pair of brackets; each bracket being mounted on an opposing molar in a patient's mouth. A resiliently flexible wire with a device intermediate its length for producing corrective forces has a torquing band transversely mounted thereon. The torquing band is securable by an elastic device to a receiving unit mounted on the lingual side of each bracket, so as to bear both forward and laterally against the receiving unit for transmitting correctional forces therebetween. A bracket is provided having a receiving unit with planar surfaces capable of bearing flushly against a torquing band having planar forward and lateral bearing surfaces.

9 Claims, 9 Drawing Figures

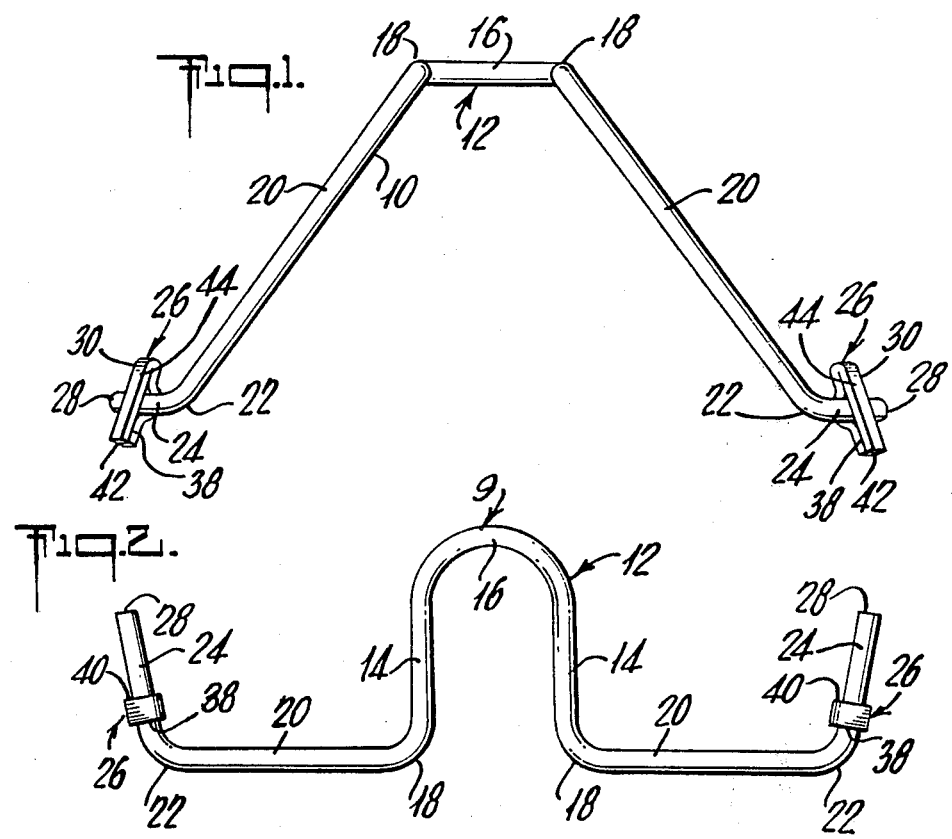

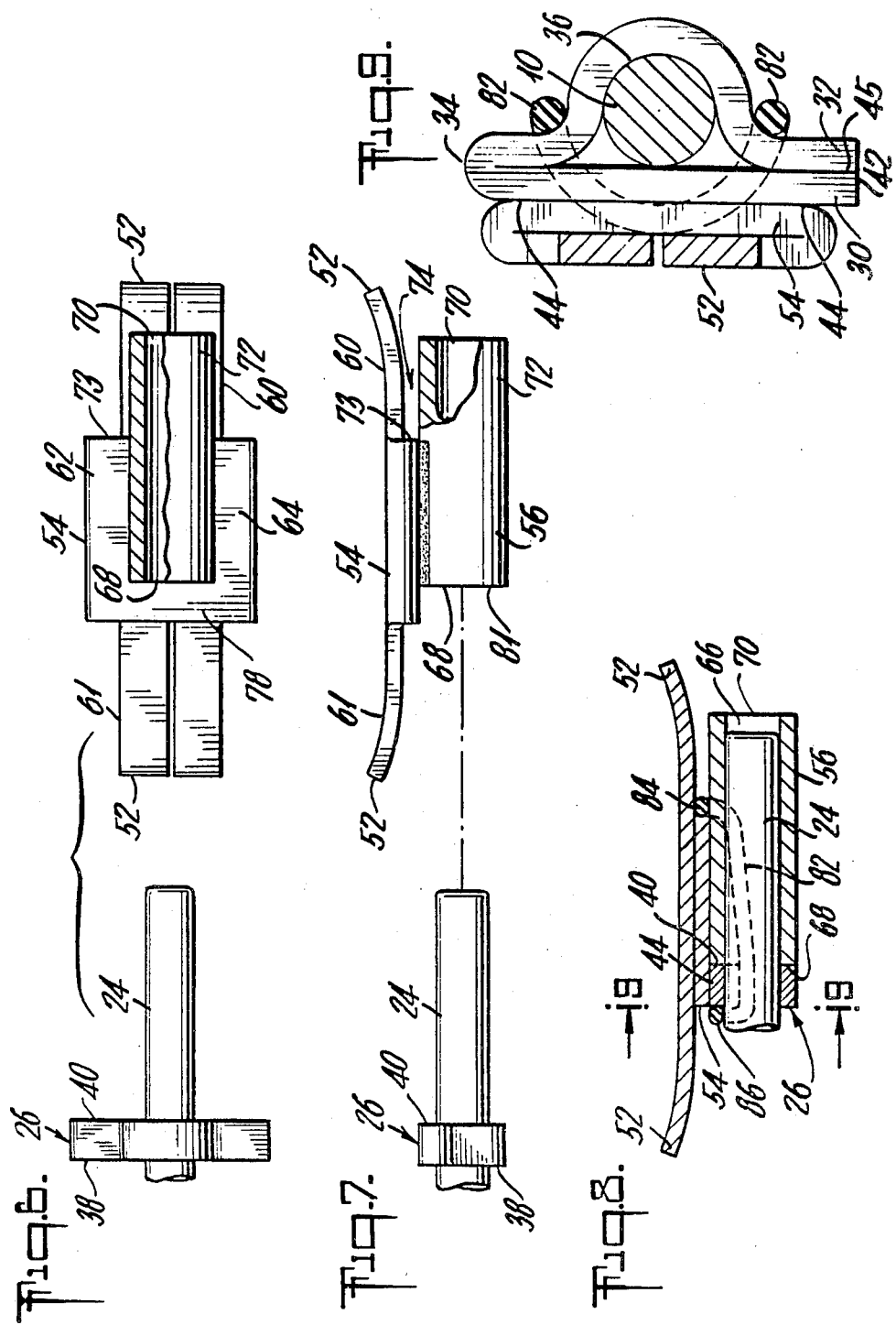

ORTHODONTIC PALATAL ARCH WIRES FOR ACCURATE TRANSMITTAL OF CORRECTIONAL FORCES

DESCRIPTION

BACKGROUND OF THE INVENTION

1. Field of the Invention

This invention relates generally to orthodontic appliances and more particularly to an orthodontic palatal arch wire capable of accurately transmitting correctional forces to a pair of brackets mounted on opposing molars.

2. Description of the Prior Art

A palatal arch wire is employed by orthodontists to apply corrective forces to misaligned molars by exerting directional control over the pair of brackets to which it is attached; each bracket being mounted on an opposing molar for transmission of the corrective forces therethrough to the tooth. The types of forces desirably exerted include expansion, contraction, intrusion, torquing and/or rotating.

Considerations present in developing a suitable palatal arch wire include the ease of adequately attaching each of the end portions to a corresponding molar bracket and the ease of removal therefrom. The desire for easy removal of the arch wire from the bracket deters the use of certain forms of attachments, such as soldering, welding, or crimping of the bracket around the wire.

A problem that arises with the use of palatal arch wires is the inadequate control over the brackets resulting from the improper anchorage of the wire to the brackets. Thus, this problem occurs when corrective forces produced by the arch wire are not fully transmitted therethrough to each of the brackets because of motional slippage between the wire and brackets. For example, untransmitted angular movement or rotation of the wire relative to a bracket occurs when the bracket utilizes an open-ended tube having a circular bore therethrough as a receptacle for a similarly dimensioned circular arch wire. The wire can twist or rotate freely within the tube when a torquing force is applied through the arch wire. Corrective forces are efficiently produced in arch wires having compressible loops or spring devices intermediate their lengths; however, until the present invention these arch wires have provided certain disadvantages, with respect to their form of anchorage to the molar brackets.

The problem of motional slippage in palatal arch wires has been recognized in the prior art. Examples of patents addressing this problem are U.S. Pat. No. 3,162,948 to Gerber and U.S. Pat. No. 3,792,529 to Goshgarian. Gerber, in the aforesaid patent, provides for a palatal arch wire capable of contracting or spreading the dental arch by means of a spring device. The arch wire is inserted near each of its ends into a tube attached to a mounting bracket. Gerber suggests inserting an arch wire having a polygonal shape into an open-ended hollow tube that has a mating polygonal cross-sectional bore. This permits interengagement and a torsional locking arrangement, so as to prevent angular movement about the longitudinal axis of the tubes.

The arch wires described in the aforesaid patent to Goshgarian have an adjustable U-shaped integral compressible loop intermediate its length. In addition, the terminal ends of the wire are bent over double to form rectangularly shaped inserts. Goshgarian suggests frictionally fitting each of these inserts into the bracket opening and relying on the springlike quality of the arch wires to cause the inserts to be firmly retained therein, thereby minimizing the twisting of the end portions within the bracket.

Each of these structures, Gerber's and Goshgarian's, for securing the arch wire to the bracket provides disadvantages. The use of a polygonally shaped wire and tube capable of interengagement requires fabrication of these items within relatively small dimensional tolerances to achieve the desired locking arrangement. Similarly, the rectangularly shaped insert requires a specially fabricated receiving member on the band to frictionally engage the unconventional terminal end. This frictional engagement is responsible for the production of undue force in the tooth during insertion and removal of the insert from the receiving member.

Thus, there is a need for a palatal arch wire, having a circular cross-sectional dimension, that is easily attachable to, and yet easily removable from, a receiving member having a circular bore therethrough; while at the same time, being capable of preventing motional slippage of the wire relative to the bracket during securement.

Accordingly, it is a principal object of this invention to provide for an arch wire capable of being easily attached to a pair of brackets in such a manner that the correctional forces produced by the arch wire are precisely applied therethrough to the teeth without slippage of the arch wire relative to the bracket.

It is a further object of the present invention to provide a molar bracket that cooperates with the palatal arch wire for accurate transmission of the correctional forces.

It is another object of the present invention to provide for a simply manufactured arch wire which is easily attachable to, and removable from, the molar bracket.

An additional object of the present invention is to provide an arch wire that is inexpensive to manufacture and has widespread applicability.

SUMMARY OF THE INVENTION

The objectives of the present invention are achieved by using a novel orthodontic arch wire for providing adjustable directional control over a pair of brackets, each of which are mounted through its base portion on an opposing molar in the patient's mouth. Each bracket has a receiving unit composed of a receiving member of open-ended hollow tube and a platform portion. Each hollow tube is mounted on the platform portion located on the lingual side of the corresponding bracket. An end portion of the wire is inserted into each hollow tube.

A torquing band is transversely mounted on and secured to the arch wire proximate to each end. Upon complete insertion of an end into the tube, the torquing band bears forwardly against the inlet end of the tube and laterally against the lingual surface of the platform portion for transmission of corrective forces from the wire to the bracket. The outlet end of the tube is cantilevered from the platform portion over the base portion so as to provide a slot or recess having a pivot point for looping part of an endless elastic device or ligature wire. An opposing pivot location is provided at the junction of the torquing band and arch wire. The torquing band prevents the arch wire from twisting and, upon proper securement with the elastic device, from moving longitudinally forwardly or rearwardly relative to the tube, and thus requires the accurate transmission of the corrective forces to the band.

BRIEF DESCRIPTION OF THE DRAWINGS

The foregoing and other objects, characteristics and advantages of the present invention will be more clearly understood from the following description when read in conjunction with the accompanying drawings in which:

FIG. 1 is a front elevational view of the arch wire of the present invention;

FIG. 2 is a top plan view of the arch wire shown in FIG. 1;

FIG. 3 is bottom plan view showing the arch wire secured to opposing molar brackets by two elastic devices, one of which is hown in section;

FIG. 4 is a perspective view of an end portion of the arch wire and a bracket aligned prior to engagement;

FIG. 5 is a perspective view of the end portion of the arch wire secured by an elastic device to a bracket;

FIG. 6 is an elevational view of the end portion of the arch wire and bracket prior to engagement;

FIG. 7 is a top plan view of the end portion and bracket prior to engagement;

FIG. 8 is a longitudinal sectional view of the engaged arch wire and bracket secured by an elastic device; and FIG. 9 is a cross-sectional view taken along line 9—9 of FIG. 8.

DESCRIPTION OF THE PREFERRED EMBODIMENT

Referring now to the drawings wherein reference numeral 9 generally indicates an orthodontic arch wire in accordance with the present invention. The arch wire 9 is preferably formed from stainless steel wire, generally indicated by the reference numeral 10, having a circular cross-sectional configuration with a diameter of 0.036 inches. Other resilient materials and dimensions can, however, be utilized. The wire 10 has a length that is at least adequate to extend from one molar to the opposing molar in an archlike shape across the palate. As shown most clearly in FIGS. 1-3, the wire 10 has disposed intermediate its length a U-shaped projection or loop, generally indicated by the reference numeral 12, extending posteriorly in a horizontal plane at the summit of the arch. The U-shaped projection 12 includes two opposing arm segments 14 interconnected by an arcuate segment 16. The end of each arm segment 14 is joined at a bend 18 to a leg portion 20 extending downwardly and outwardly from the loop 12. Each of the leg portions 20 terminates in a bend 22 having an end portion 24 gently sloping outwardly in a posterior direction from the bend 22. The arch wire 10 is symmetrical with respect to a vertical plane passing through the center of the arcuate segment 16. The leg portions 20 form, preferably, an angle of about 40° with said vertical plane of symmetry.

The U-shaped projection or loop 12 is capable of providing the correctional forces discussed in the aforementioned Goshgarian patent, incorporated herein by reference with respect to the description of the forces produced in the wire as a result of the manipulation of the open loop. For example, the rotation of the molars can be obtained by expanding or compressing the loop so as to obtain a desired spring force; the wire being easily removed from the patient's mouth for adjustment of the loop. Similarly, torquing tension can be applied to the molars by bending the U-shaped loop at a transverse angle relationship to its normal plane prior to adjusting the spread of the loop. It should be noted, however, that the present invention is not limited to a compressible U-shaped open loop but is applicable to any arch wire having a means intermediate its length for producing a corrective force in the end portions of the arch wire, e.g. closed loops and multiple loops.

Each of the end portions 24 is equipped with a means for transmitting corrective forces, also referred to as a torquing band, and generally indicated by the reference numeral 26, that is welded or otherwise similarly fixedly secured proximate to the ends 28 of the wire 10. Each torquing band 26 is mounted transverse to the longitudinal axis of the corresponding end portion 24 and forms, preferably, an angle of about 20° with the longitudinal axis of the corresponding leg portion 20. The torquing band 26, as shown most clearly in FIG. 9, is comprised of two overlying and aligned portions; an outer portion 30 and an inner portion 32, interconnected by a bend 34 therebetween. Intermediate the length of the inner portion 32 is a U-shaped channel 36 sized to receive the cross-sectional area of the wire 10 therein. The two portions 30, 32 align to form anterior 38, posterior 40 and bottom 42 surfaces that are planar (FIGS. 2 and 6-9). As shown most clearly in FIGS. 1 and 9, the outer portion 30 has a planar and unitary outer bearing surface 44. The distance between the outer bearing surface 44 and inner surface 45 is referred to as the thickness of the torquing band 26. The width of the torquing band 26 corresponds to the distance between the bottom surface 42 and the outermost portion of the bend 34.

The torquing band 26 may be shaped by bending a uniformly dimensioned slender metal ribbon having a rectangular cross-sectional area near its center so as to form the two portions 30, 32 with the inner portion 32 being slightly longer than the outer portion 30. The U-shaped channel 36 is formed in the longer inner portion 32 and the band 26 is fitted around the wire 10 and brazed and/or welded onto the end portion 24. The two portions 30, 32 overlie and abut one another along the inner surface 45 except in the area of the U-shaped channel 36.

Prior to the installation of the arch wire 9 into the upper jaw of the patient's mouth, a bracket, generally indicated by the reference numeral 46, is mounted on each of two opposing molars 48. Each bracket 46 can be either mounted on a direct bonding base such as a wire mesh and secured to a molar (not shown) by an appropriate adhesive, or as shown in FIG. 3, the bracket 46 can be secured, such as by welding, to a band 50 which is in turn mounted on a molar 48. The bracket 46, shown most clearly in FIGS. 4 and 6-8, is preferably made from stainless steel and includes a base portion 52, a platform portion 54 and a receiving member 56. The base portion 52 is an elongated strip curved at each of its ends so as to conform to the shape of the lingual portion of the band 50. The base portion 52 may be severed medially, as shown, at each end segment 60, 61 so as to form two parallel strips which facilitate shaping for proper joining to a molar band 50. The rectangular platform portion 54 is mounted on the lingual side of the base portion 52, intermediate its length so as to extend across its width with a portion projecting above 62 and below 64 the base portion 52.

The receiving member is a hollow tube 56, rigidly secured, usually by soldering or welding, on the platform portion 54 so as to extend longitudinally in a proximal-distal direction when in the mouth and, therefore, substantially perpendicular to the longitudinal axis of the corresponding molar 48. The combination of the platform portion 54 and receiving member 56 is referred to as the receiving unit. The tube 56 is cylindrical, open-ended and has a uniform central bore 66 extending therethrough from the inlet end 68 to the outlet end 70. The bore 66 is dimensionally sized to receive the end portion 24 of the wire 10 snugly therein.

The tube 56 is mounted on the platform portion 54 with its outlet portion 72 extending beyond the platform edge 73 so as to be cantilevered. A recess or slot 74 is defined on three sides by the cantilevered outlet portion 72, the end segment 60 of the base portion 52 and the edge 73 of the platform portion 54. The inlet end 68 of the tube 56 is mounted so as to provide a ledge 78 between the edge 80 of the platform portion 54 and the inlet end 68 that is sized to accommodate at least a substantial portion of the width of the torquing band 26.

Referring now to FIGS. 4–9, the end portions 24 of the wire 10 are inserted into the inlet opening 81 of the tube 56 until the posterior planar surface 40 of the torquing band 26 bears forwardly against the planar inlet end 68 of the tube for transmitting forces to the bracket and for preventing further entry of the wire 10 therein; at which time the arch wire 9 is considered engaged with the bracket 50. Preferably, the perpendicular distance from the surface of the platform portion 54 to the inlet opening 81 is equal to the thickness of the torquing band 26 so as to facilitate positioning of the end portion 24 into the receiving member 56 with the outer bearing surface 44 and posterior surface 40 bearing against the receiving unit. Furthermore, during engagement the bearing surface 44 of the torquing band 26 bears laterally outward against the surface of the ledge 78 on the platform portion 54. The ledge 78 is sized to accommodate at least enough of the bearing surface for transmittal of torsional and lateral forces through the platform portion to the bracket. Preferably, the bearing surface 44 and the surface of the platform portion 54 are planar so as to abut flush against one another during engagement. The width of the torquing band 26 extends above and below the wire 10, so that any clockwise or counterclockwise rotation of the end portion 24 is transmitted to the corresponding molar band 50. The ends 28 of the wire 10 terminate, preferably, within the tube 56 (FIG. 8); however, the wire 10 may extend beyond the outlet end 70 so that the additional length could be used for additional orthodontic purposes. Thus, the points of termination of the wire 10 are dependent on the lengths of the end portions 24, the lengths of the receiving members 56, and the positions of the torquing bands 26.

It is apparent that there are surface configurations, in addition to planar that are suitable for the inlet end 68, platform portion 54, posterior 40 and outer bearing surfaces 44 of the torquing band 26 provided adequate forward and lateral surface contact is provided for transmittal of the corrective forces.

During engagement, the leg portions 20 extend towards the roof of the mouth, or in other words, towards the apex of the palatene process in the superior maxillary bone, with the U-shaped loop 12 being adjacent to the roof so as not to interfere with normal tongue movement. An effective position for the arch wire 9 occurs when the leg portions 20 define a transverse plane extending substantially through the longitudinal center lines of the opposing molars 48.

Also during engagement, as shown in FIGS. 5, 8 and 9, the end portions 24 are secured in the tube 56 by means of an endless elastic device 82, such as a rubber band, formerly positioned around the arch wire (FIG. 4), stretched around two opposite pivot points 84, 86. The first pivot point 84 is formed in the slot 74 at the edge 80 of the platform portion 54. The second pivot point 86 is the junction of the end portion 24 and the anterior surface 38 of the torquing band 26. The elastic device 82 is looped around each junction point 84, 86 so as to form two opposing U-shaped loops 88, 90 interconnected by two arm portions 92, 94 extending along the top and bottom of the tube 56, respectively. The elastic force exerted by the elastic device 82 mounted on the affixed bracket 46 draws the slidable end portion 24 of the wire 10 into the bore 66 of the tube 56 up to the posterior surface 40 of the torquing band 26 and retains it therein.

The inverted T-shaped junction 86 of the torquing band 26 and the wire 10 thus provides a means for gripping the wire 10 and urging it into the receiving member 56.

It should be noted that the anchorage provided by the cooperation of the torquing band with the end portions, the receiving unit and the elastic device provides for the transmissability of the corrective force produced by the manipulation of the arch wire to the corresponding molar band. Specifically, manipulation of the wire to produce torquing induces a clockwise or counterclockwise twisting of the wire which is transmitted to the bracket by the upper or lowr part of the outer bearing surface of the torquing band bearing against the surface of the platform portion of the bracket. Expansion is provided by the outer bearing surface of the torquing band bearing laterally outward against the surface of the platform portion and the end portion of the arch wire pushing laterally outward against the tube. Contraction is provided by the end portions pushing laterally inward against the tube. Rotation of an upper molar is provided by the end portion bearing against the receiving member in cooperation with the torquing band bearing against the inlet end of the receiving member. Extrusion is provided by the end portion pushing downward against the tube while intrusion is provided by the end portion pulling upward on the receiving member. During the application of these corrective forces the elastic device prevents the arch wire from slipping out from the bore in the tube.

It has been found that the employment of the arch wire of the present invention results in accurate transmission of corrective forces to the molar bracket without motional slippage. Principal advantages of the arrangement represented are that the torquing band eliminates the prior art requirement of an interlocking arrangement between the end portion and receiving member to reduce motional slippage, and that the end portions can be inserted or removed from the receiving members without the application of undue force to the tooth.

I claim:
1. An orthodontic palatal arch wire for directional control over a pair of brackets, each of the brackets being mounted on an opposing molar in a patient's mouth and including a receiving unit on the lingual side thereof, comprising in combination:
   a resiliently flexible wire having a length at least as great as the palatal distance between the pair of brackets, each end portion of said wire being snugly insertable into said receiving unit;

means disposed intermediate to the length of said wire for creating corrective forces in said end portions of said wire; and a torquing band transversely mounted on said wire proximate to each end, said torquing band being securable external to and in contact with said receiving unit after insertion so as to bear both forwardly and laterally against the receiving unit for transmitting said corrective forces therebetween.

2. The arch wire as claimed in claim 1 wherein said means comprises a U-shaped loop configured for producing corrective forces in said end portion.

3. The arch wire as claimed in claim 2 wherein said wire has a circular cross-sectional configuration and the receiving unit includes a hollow open-ended tube having a bore therethrough for receiving an end portion of said wire, and a platform portion having said receiving member mounted thereon, said torquing band bearing forwardly against the inlet end of the tube and laterally against the platform portion during securement.

4. The arch wire as claimed in claim 3 wherein said torquing band includes an outer portion having a substantially planar outer surface for bearing against the platform portion and an inner portion joined to said outer portion at a bend, said inner portion having a U-shaped channel intermediate its length for receipt of the arch wire therein, said wire being sandwiched between said outer and inner portions.

5. The arch wire as claimed in claim 3 wherein said torquing band has a planar posterior surface for bearing against the inlet end of the receiving tube and a planar outer bearing surface for bearing against the platform portion.

6. The arch wire as claimed in claim 5 wherein said arch wire upon insertion into said receiving member is fixedly securable to said torquing band by an elastic device having a portion thereof looped around a part of the bracket and another portion looped around the junction of said wire and said torquing band.

7. A dental bracket for use with an arch wire having a torquing band, comprising in combination:

an elongated base portion adapted to be attached to a tooth;

a platform portion disposed intermediate to the length of said base portion; and a receiving member mounted on said platform portion and having a bore therein adapted to receiving an end portion of an arch wire, said receiving member having an outlet portion cantilevered from one end of said platform portion and an inlet end proximate to the opposite end of said platform portion, said platform portion having a planar ledge end, said opposite end of said platform portion adapted to abut flushly against a planar bearing surface of the torquing band, and said inlet end having a planar surface for abutting flushly against the posterior surface of the torquing band.

8. The dental bracket as claimed in claim 7 wherein said receiving member includes a cylindrical tube having a bore extending therethrough, said bore having a circular cross sectional configuration.

9. The dental bracket as claimed in claim 8 wherein the distance from the ledge surface to the circumference of the bore at the inlet end is predetermined to coincide with the thickness of the torquing band.

* * * * *